US00PP37362P2

(12) United States Plant Patent
Van Haaster

(10) Patent No.: US PP37,362 P2
(45) Date of Patent: Apr. 7, 2026

(54) ***DAHLIA* PLANT NAMED 'DDAHCHASTP'**

(50) Latin Name: ***Dahlia* hybrid**
Varietal Denomination: DDAHCHASTP

(71) Applicant: Ans Van Haaster, Hillegom (NL)

(72) Inventor: Ans Van Haaster, Hillegom (NL)

( * ) Notice: Subject to any disclaimer, the term of this patent is extended or adjusted under 35 U.S.C. 154(b) by 0 days.

(21) Appl. No.: 19/025,731

(22) Filed: Jan. 16, 2025

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC . A01H 5/02; A01H 5/00; A01H 6/144; A01H 6/14
See application file for complete search history.

(56) References Cited

U.S. PATENT DOCUMENTS

PP25,798 P3 * 8/2015 Nielsen ..... A01H 6/14 Plt./321

OTHER PUBLICATIONS

Dümmen Orange Hypnotica Rose Swirl retrieved on Jul. 28, 2025 at https://emea.dummenorange.com/app/en/products/usa/dahlia/hypnotica-rose-swirl/PAT_73966, 2 pages. (Year: 2025).*

National Dahlia Society Dahlia Classification and Formation retrieved on Jul. 28, 2025 at https://www.dahlia-nds.co.uk/about-dahlias/classification/, 19 pp. (Year: 2025).*

RHS Dahlia Dalina Maxi Salinas retrieved on Jul. 28, 2025 at https://www.rhs.org.uk/plants/374216/dahlia-dalina-maxi-salinas-(-dasyvogtyve-pbr)-(dalina-maxi-series)-(d)/details, 4 pp. (Year: 2025).*

* cited by examiner

*Primary Examiner* — June Hwu

(57) ABSTRACT

A new and distinct cultivar of *Dahlia* plant named 'DDAHCHASTP' is disclosed, characterized by red-purple double flowers with closed, dark purple centers when opening, then develop white "halos" at the base when mature. Plants have upright habits and dark green foliage. The new variety is a *Dahlia*, typically produced as an ornamental plant.

2 Drawing Sheets

Figure 1:
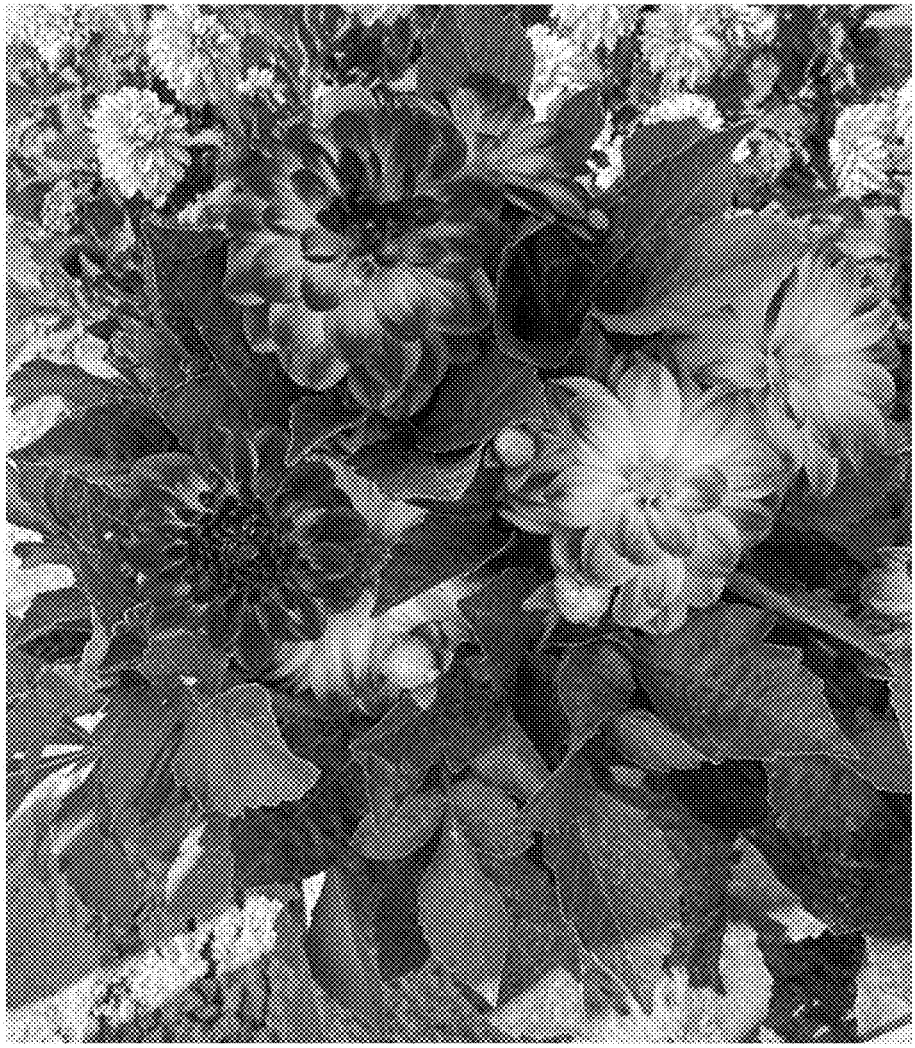

Latin name of the genus and species: *Dahlia* hybrid.
Variety denomination: 'DDAHCHASTP'.

BACKGROUND OF THE INVENTION

The new *Dahlia* cultivar is a product of a planned breeding program conducted by the inventor, Ans van Haaster in Hillegom, the Netherlands. The objective of the breeding program was to produce useful new *Dahlia* varieties for ornamental horticultural production. The crossing resulting in this new variety was made in August 2020.

The seed parent is the unpatented variety *Dahlia* 'Rose Swirl'. The pollen parent is the unpatented variety *Dahlia* 'Purple Bicolor'. The new variety was discovered in August 2021 by the inventor in a group of seedlings in Hillegom, the Netherlands. Asexual propagation of *Dahlia* was performed by vegetative cuttings in September 2021, at the same location in Hillegom, the Netherlands. After selection of the new variety, extensive confidential testing has been performed to determine and define the desirable characteristics of the new variety.

SUMMARY OF THE INVENTION

The cultivar 'DDAHCHASTP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DDAHCHASTP'. These characteristics in combination distinguish 'DDAHCHASTP' as a new and distinct *Dahlia* cultivar:

1. Young red-purple flowers have closed, dark purple centers.
2. Flower centers open with maturity, revealing yellow pollen.
3. Mature flowers develop white "halos" from the base.

PARENT COMPARISONS

Plants of 'DDAHCHASTP' are similar in some horticultural characteristics to the seed parent. The new variety, however, differs in the following:

1. Flower color of the new variety is darker than the flower color of the seed parent.
2. Main flower color of the new variety is purple with white as a secondary color, while the main flower color of the seed parent is white with red-purple as a secondary color.

Plants of 'DDAHCHASTP' are similar in some horticultural characteristics to the pollen parent. The new variety, however, differs in the following:

1. Flower color of the new variety is purple and white, while the flower color of the pollen parent is various shades of purple with no white.

2. Plants of the new variety are not as vigorous as plants of the pollen parent.
3. Leaf margins of the new variety are not as serrated as leaf margins of the pollen parent.

COMMERCIAL COMPARISONS

Plants of 'DDAHCHASTP' are similar in some horticultural characteristics to the variety *Dahlia* 'Maggiore Fun Rose Bicolour', unpatented. The new variety, however, differs in the following:

1. Flower color of the new variety is more purple, while the flower color of this comparator is more fuchsia.
2. Petal shape of the new variety is oval, while the petal shape of this comparator is pointed.
3. Flowers of the new variety have white "halos", while flowers of this comparator have yellow "halos".

Plants of 'DDAHCHASTP' are similar in some horticultural characteristics to the variety *Dahlia* 'Dasyvogtyve' U.S. Plant Pat. No. 25,798. The new variety, however, differs in the following:

1. Foliage color of the new variety is lighter than the foliage color of this comparator.
2. Flower centers of the new variety are more open, exposing the pollen, than flower centers of this comparator.
3. Flower color of the new variety is more purple and white, while the flower color of this comparator is more pink and white.

BRIEF DESCRIPTION OF THE PHOTOGRAPHS

The accompanying photograph in FIG. 1 illustrates in full color a typical plant of 'DDAHCHASTP' 80 days from planting, grown outdoors in a trial field.

Figure 2:
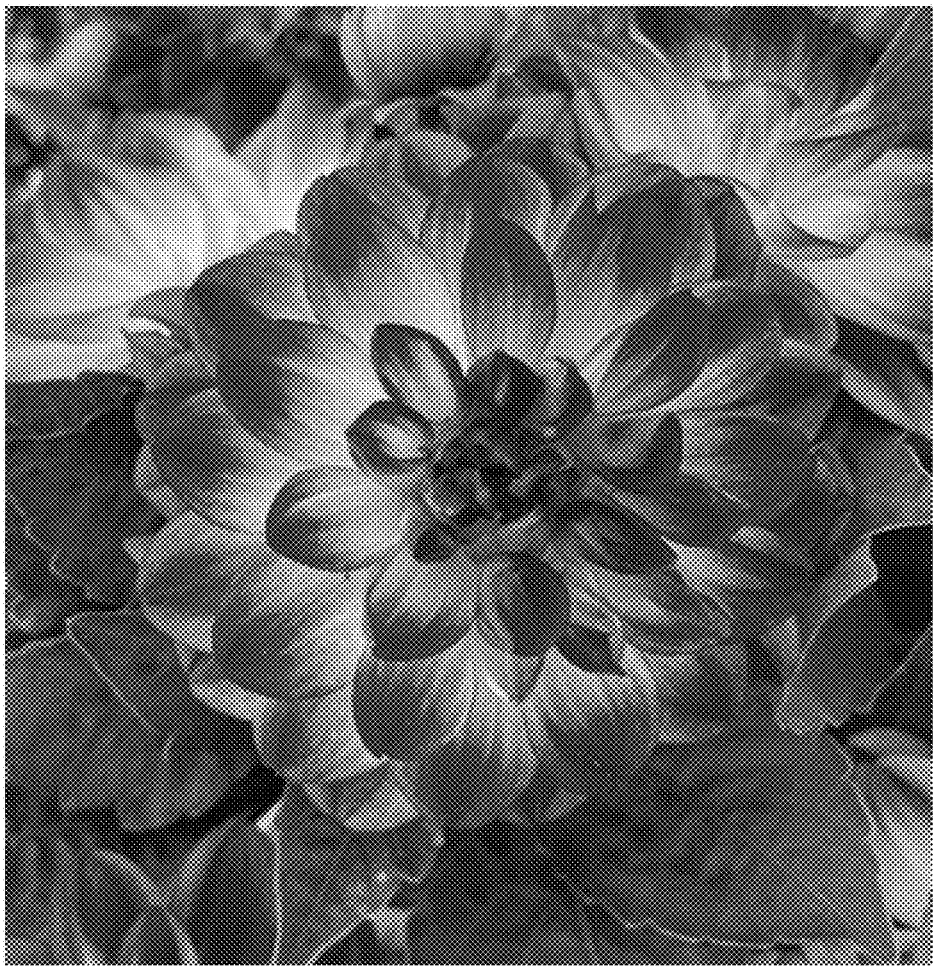

FIG. 2 illustrates a closer view of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DDAHCHASTP' plants grown in a plastic tunnel in Hillegom, the Netherlands, under natural lighting. Measurements were taken August 2024. The growing temperature ranged from approximately 15° C. to 32° C. during the days, 8° C. to 20° C. during the nights. Measurements and numerical values represent averages of typical plant types.

Botanical classification: *Dahlia* hybrid 'DDAHCHASTP'.

PROPAGATION

Propagation method: Vegetative cuttings.

Time to initiate rooting: 8 to 15 days in summer; 12 to 17 days in winter.

Root description: Fibrous and relatively shallow in the early stages of development. Roots grow more complex as the plant matures.

Tuber description: Skin firm and relatively thin, colored light brown. Inner flesh moist and firm, colored white. Colors not accurately measured with R.H.S. chart.

PLANT

Age of plant described: 80 days from a rooted cutting.

Growth habit: Upright.

Pot size of plant described: 13 cm.

Height: 35 cm.

Plant spread: 46 cm.

Growth rate: Moderate

Branching characteristics:

Length of lateral branches: 17 cm.

Diameter of lateral branches: 4 to 7 mm.

Quantity of lateral branches: 12 per main stem.

Characteristics of primary lateral branches:

*Diameter.*—0.8 cm.

*Color.*—RHS Green 137C.

*Texture.*—Smooth.

*Strength.*—Strong.

Internode length: 6 cm.

FOLIAGE

Leaf:

*Arrangement.*—Compound.

*Quantity.*—Approximately 4 per branch.

*Average overall length.*—15 cm.

*Average overall width.*—10 cm.

*Overall shape.*—Deltate.

Leaflets:

*Shape.*—Ovate.

*Quantity.*—Typically 3 leaflets per leaf.

*Length.*—3.5 to 5 cm.

*Width.*—2 to 2.5 cm.

*Apex.*—Tapered to a point.

*Base.*—Rounded, sometimes slightly cordate (heart-shaped).

*Margin.*—Serrate. Few and shallow.

*Texture.*—Smooth.

*Pubescence.*—None. Glabrous all surfaces.

*Color.*—Young foliage upper side: RHS Green 137B. Young foliage under side: RHS Green 137C. Mature foliage upper side: RHS Green 137A. Mature foliage under side: RHS Green 137B.

*Venation.*—Pattern: Reticulate-central main vein runs through the length of the leaf, with smaller lateral veins branching off from it in a feather-like pattern. Color, upper side: RHS Green 137C. Color, under side: RHS Green 137D.

Petiole:

*Length.*—3 cm.

*Diameter.*—0.2 cm.

*Color.*—RHS Green 137D.

*Texture.*—Smooth.

Stipule:

*Length.*—3.3 cm.

*Diameter.*—1 cm.

*Color*.—RHS Green 137D.
*Texture*.—Smooth all surfaces.
Leaf wings: Not present.

FLOWER

Natural flowering season: Summer to autumn.
Days to flowering from rooted cutting: 58 days.
Inflorescence and flower type and habit: Daisy-eyed double.
Position: One the same level as the foliage or slightly above foliage.
Attitude: Upward.
Rate of flower opening: 8 to 13 days from bud to fully opened flower.
Flower longevity on plant: 20 days.
Persistent or self-cleaning: Persistent.
Bud:
*Shape*.—Round.
*Length*.—2 cm.
*Diameter*.—2.5 cm.
*Color*.—RHS Red-Purple 78B.
Flower size:
*Diameter*.—11 cm.
*Depth*.—3.5 cm.
Ray florets:
*Arrangement*.—Double flower, radial symmetry.
*Length*.—4.5 cm.
*Width*.—2.5 cm.
*Quantity*.—About 77.
*Texture*.—Smooth all surfaces. Shallowly ribbed.
*Apex*.—Round.
*Base*.—Pointed.
*Shape*.—Oval.
*Margin*.—Straight, smooth.
*Longtitudinal axis shape*.—Slightly reflexing.
*Ray floret shape at midpoint*.—Weakly convex.
*Ray floret margin rolling*.—Flat.
*Color*.—When Opening, Upper Surface: RHS Red-Purple 78A (covering 75% to 90%); lower section White N155B (covering 10% to 25% of the surface); base Yellow 6C. Centermost ray florets Purple N79C. When Opening, Lower Surface: RHS Red-Purple 78C; base Yellow 6D. Centermost ray florets Purple-Violet N81A. Fully Opened, Upper Surface: RHS Red-Purple 78A (covering 20% to 50% of the surface) lower section Purple-Pink 55C and White N155B (covering 50% to 80% of the surface); base Yellow 6B. Fully Opened, Lower Surface RHS Red-Purple 78C (covering 20% to 50%); lower section White 155B flushed Purple-Pink 55C (covering 50% to 80% of the surface); base Yellow 9C.
Disc: 1 to 1.8 cm in diameter and 1 cm high.
Disc florets:
*Shape*.—Tubular.
*Apex*.—Acute.
*Length*.—About 10 mm.
*Diameter, base*.—About 1 mm.
*Number of disc florets per inflorescence*.—Average 35.
*Color*.—Apex Yellow 9A, base 7D.
Sepals:
*Quantity per flower*.—7.
*Shape*.—Oval.
*Length*.—1.5 cm.
*Width*.—0.8 cm.
*Apex*.—Round.
*Base*.—Pointed.
*Margin*.—Straight.
*Color*.—RHS Green 138A.
Peduncles:
*Strength*.—Exceptional.
*Aspect*.—very strong, mostly upright. Angle of bloom from lateral branch 12-24 degrees.
*Texture*.—Glabrous.
*Color*.—Green 137C.
*Length*.—5 to 8 cm.
*Diameter*.—7 mm.
Fragrance: Soft.

REPRODUCTIVE ORGANS

Androecium: Present in disc florets only.
Stamens:
*Number*.—5.
Anthers:
*Shape*.—Linear.
*Length*.—About 0.5 cm.
*Color*.—RHS Yellow 9A.
*Pollen*.—Color: RHS Yellow 9A. Quantity: Abundant.
Gynoecium disc florets:
Pistil:
*Number*.—1.
*Length*.—1 cm.
*Style*.—Length: 8 mm. Color: RHS Yellow 9C.
*Stigma*.—Shape: V-shaped. Color: RHS Yellow 9C. Ovary Color: RHS Yellow 9C.
Gynoecium ray florets:
Pistil:
*Number*.—1.
*Length*.—1.3 cm.
*Style*.—Length: 1 cm. Color: RHS White 155C
*Stigma*.—Shape: V-shaped. Color: RHS Yellow 6C.
*Ovary color*.—RHS Yellow 6D.

OTHER CHARACTERISTICS

Seeds and fruits: Not observed to date.
Disease/pest resistance: Neither resistance nor susceptibility to typical *Dahlia* pests and diseases observed.
Temperature tolerance: Tolerant from 1° to 38° C.

What is claimed is:

1. A new and distinct cultivar of *Dahlia* plant named 'DDAHCHASTP' as herein illustrated and described.

* * * * *